United States Patent [19]
Esparza et al.

[11] Patent Number: 5,519,208
[45] Date of Patent: May 21, 1996

[54] INFRARED AIDED METHOD AND APPARATUS FOR VENOUS EXAMINATION

[76] Inventors: Joel Esparza, 4930 National Ave., #7, San Jose, Calif. 95124; Robert S. Smith, 1263 Emory St., San Jose, Calif. 95126

[21] Appl. No.: 315,128

[22] Filed: Sep. 29, 1994

[51] Int. Cl.⁶ .................................................. G01J 3/50
[52] U.S. Cl. ...................... 250/226; 250/341.8; 250/574; 128/664
[58] Field of Search ........................ 250/226, 574, 250/561, 330, 339.11, 341.8, 339.14, 343; 128/664, 673, 692

[56] References Cited

U.S. PATENT DOCUMENTS

| | | | |
|---|---|---|---|
| 3,514,174 | 5/1970 | Gans et al. | |
| 4,817,622 | 4/1989 | Pennypacker et al. | 250/330 |
| 4,975,581 | 12/1990 | Robinson et al. | 250/339.11 |
| 5,204,774 | 4/1993 | Owen et al. | 359/418 |
| 5,233,465 | 8/1993 | Wheatley et al. | 359/359 |
| 5,248,874 | 9/1993 | Raverdy | 250/214 VT |

*Primary Examiner*—Edward P. Westin
*Assistant Examiner*—Que T. Le
*Attorney, Agent, or Firm*—Robert Samuel Smith

[57] ABSTRACT

A method and apparatus for gaining intravenous access including a source of radiation for irradiating an area of the patient wherein the radiation has a wavelength such that the radiation is absorbed in areas containing veins and reflected in all other areas thereby forming a view which is seen through a screen to be the area where venous structure appears as dark lines thereby enabling a user to position the tip of a hypodermic needle at an appropriate location for drawing blood. In one arrangement, the apparatus is mounted on the head of the user. In another arrangement the device is mounted on a floor stand. In another embodiment, the apparatus is equipped with an image intensifier. In another embodiment, a mirror is provided enabling the user to view the selected area and the image simultaneously.

24 Claims, 2 Drawing Sheets

# INFRARED AIDED METHOD AND APPARATUS FOR VENOUS EXAMINATION

BACKGROUND

1. Field of the Invention

This invention relates to visual examination of the features of the human body such as the venous system and particularly to improvements in the method of gaining intravenous access by enhancing the view of the venous system by infrared illumination.

2. Prior Art and Information Disclosure

The difficulties of gaining intravenous access such as for drawing blood, intravenous fusion, etc., are well known to vary from one patient to another. Some patients have very prominent veins and this situation simplifies the procedure although, even for some of these patients, their veins have a tough resiliency that makes the veins difficult to penetrate with a hypodermic needle. In the context of this specification, the term, hypodermic needled, will be understood to mean any access device such as a syringe with needle for drawing blood, intravenous cathater, etc. In other patients, the veins are small, deepset, and scarcely visible so that gaining intravenous access is very unpleasant for both the practitioner and the patient. The complexion of the patient can be another troublesome factor. For example, the veins of Afro-Americans are not nearly as visible as the veins of many other patients which hinders the process of finding a vein and drawing blood therefrom. Infants have immature vacular development. Obese patients have venous structure that is difficult to penetrate. At the very least, these complications can greatly increase the stress experienced by the patient. At worst, delays in gaining intravenous access can result in death.

Numerous studies have been reported on the use of infrared illumination to noninvasively examine the venous system. These studies have been confined to the use of black and white infrared photography, defined as the technique of focussing an infrared image onto an emulsion.

Two approaches are used in black and white infrared photography.

In one approach, the subject producing the image reflects varying amounts of infra red radiation falling on it.

In another approach, the subject can emit luminescence in the infrared range when illuminated with visible light.

Noninvasive studies of the vascular system using infra red photography have resulted in some well known observations as discussed in the publication "Medical Infrared Photography" published by the Kodak Corp., Rochester, N.Y. which is hereby incorporated by reference into this specification.

In particular, it has been found that the actinic band of infrared has been the most useful for medical infrared photography. The actinic band lies in the range from 700 to 900 nanometers. This is the range of the near infra red. It has been found in studies using black and white infrared photography, that skin and superficial tissues reflect most of the radiation in this range of the spectrum while the blood absorbs much of this radiation. This effect results in photographs of the body in which the veins stand out as dark prominent lines against a light background as illustrated by comparing the arm shown in FIG. 1A irradiated with normal light to the same arm shown in FIG. 1A irradiated with infrared.

Various components including mirrors and filters for infrared radiation have been disclosed.

For example, U.S. Pat. No. 5,233,465 to Wheatley et al discloses a polymeric multilayered film which reflects wavelengths of light in the infrared while being substantially transparent to wavelengths in the visible spectrum. The wavelength is selected by appropriate selection of the "optical thickness" of the multilayers defined as the physical thickness multiplied by the index of refraction.

U.S. Pat. No. 3,514,174 to Gans discloses a multilayer interference transmittance filter for use in the infrared region of the spectrum.

Filters and mirrors operating at selective wavelengths can be custom made and purchased from the Rolyn Optics Co., Covina, Calif.

Devices have been developed which intensify images formed by infrared radiation. These image intensifiers are incorporated into "night vision goggles" disclosed in the patent literature.

For example, U.S. Pat. No. 5,248,874 to Raverdy discloses an image intensifier tube having a connected brightness curve.

U.S. Pat. No. 5,204,774 to Owen et al discloses a night vision goggle with an achromatic lens assembly.

"Liquid Crystals, Applications and Uses" by Birendra Bahadur, vol. 1, chapter 16, 1990, published by World Scientific, discloses construction of image intensifiers. FIG. 4 is a sectional view of an image intensifier of the prior an showing the incident image on cover 52, transparent conductive electrodes 54, photoconductor 56, light block 58, dielectric rain or 60, liquid crystal alignment films 62, liquid crystal 64, cover 52.

None of the cited art discloses or suggests the adaptation of these technologies to the act of gaining intravenous access fox the purpose of eliminating the trauma associated with locating a suitable vein.

THE INVENTION

OBJECTS

It is an object of this invention to provide a method and apparatus for gaining intravenous access from a patient that is less stressful than the method of the present state of the art. In pursuing this objective, it is recognized that some patients have veins that are not prominent or otherwise difficult to locate and the method of this invention facilitates locating these veins. It is a further object of this invention that, once an attendant locates the vein, he may then position the tip of a hyperdermic needle close to the point of entry with improved accuracy and therefore decreased trauma experienced by the patient.

SUMMARY

This invention is directed toward a method for gaining intravenous access in which an apparatus presents a view of an area of the patient (e.g., arm or leg) wherein veins are clearly delineated. An operator is thereby provided with a visual guide to locate the tip of a hypodermic needle proximal to the site of the vein.

In one embodiment, the apparatus includes a lamp arranged to illuminate a surface area of the patient with radiation having a selected wavelength that is reflected by all of the surface area except where veins are located. The apparatus also includes a viewing screen through which the user views the illuminated area. The viewing screen has a transmittance filter which transmits radiation having the selected wavelength and effectively blocks all other radiation. The venous system viewed through the screen appears as dark lines that clearly stand out enabling the operator to locate the hypodermic needle at the appropriate point of entry.

In one version of the invention, the apparatus is attached to a headband worn by the user. In another version, the apparatus is detachably mounted on a floorstand.

For some venous systems, the optimum wavelength will be in the range, between about 400 to 700 nm which is a visible range and further enhancement of the image is not necessary.

Other venous systems require the optimum wavelength for differentiating between venous and non venous areas to be in the range between 700 and 900 nm so that images formed therefrom are not visible. For this situation, the apparatus includes an image intensifier to more clearly delineate the venous structure.

In another embodiment, the apparatus includes a pair of mirrors positioned such that the operator views an image of the patient's limb with delineated veins along side the actual limb as an aid to positioning the hypodermic needle in the appropriate location.

An LED located on the needle about ¼ inch from the tip and emitting light having wavelength readily discernible through the projection system of the apparatus is a further aid to maintaining registration between the tip and point of entry.

DRAWINGS

DESCRIPTION OF A PREFERRED MODE

Figure 1:
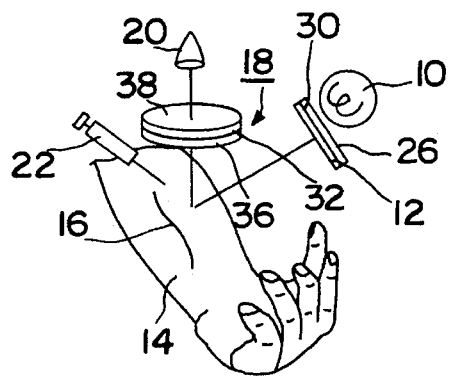
FIG. 1 shows the apparatus of this invention arranged to aid in locating an insertion point.

Turning now to a discussion of the drawings, FIG. 1 shows a lamp 10 with a transmittance filter 12 irradiating a forearm 14 of a patient. Veins 16 in the arm are delineated by selection of the passband wavelength of the transmittance filter 12 which is between 400 and 900 nm. The illuminated forearm 14 is viewed by an observer 20 through an imaging means 18 including a second transmittance filter 36 mounted on the support surface 32 of a transparent substrate 36. Second transmittance filter 38 has a passband identical to filter 12. The second filter 36 eliminates any extraneous light from sources other than the lamp 10. The observer is thereby guided to position the tip of a hypodermic needle 22 against the delineated vein 16.

Figure 5:
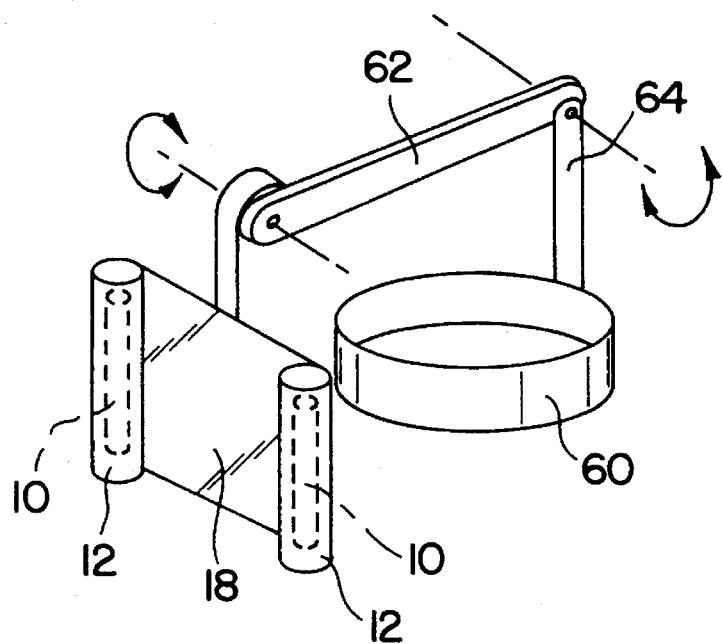
FIG. 5 shows the apparatus arranged for mounting on the head of a user.
Figure 6:
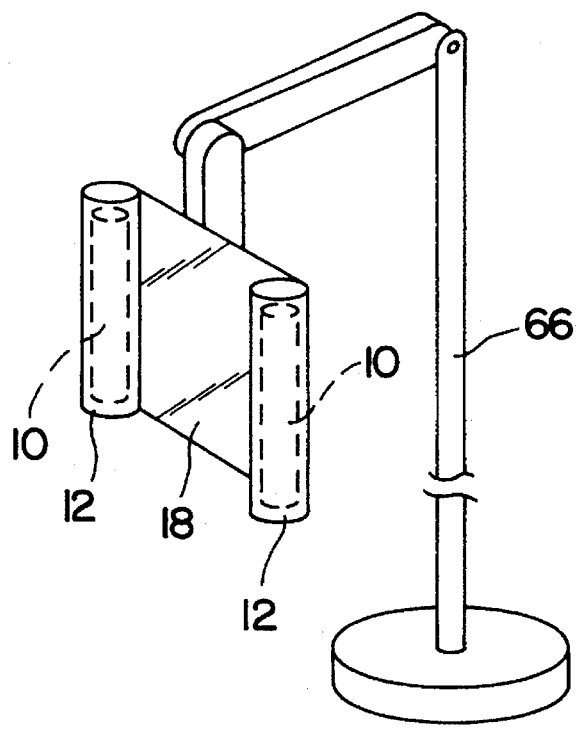
FIG. 6 shows the invention mounted on a floor stand.

FIG. 5 shows the lamp 10 with filters 12 and 18 mounted on a headband 60 by cantilever arms 62. FIG. 6 shows the lamp 10 with filters 12 and 18 mounted on a floor stand 66. These devices for mounting the viewing apparatus enable the operator to use both hands for bringing the needle into the required position relative to the venous structure.

In another arrangement, (not shown) the lamp 10 with filters 12 and 18 are supported on a handle which is hand held.

Filter 12 is a multilayer transmittance filter supported on glass substrate 26 whose support surface 30 is contoured to focus radiation from lamp 10 onto forearm 14.

Imaging means 18 is a multilayer transmittance filter 36 supported on glass substrate 38 whose support surface 32 is contoured to magnify the image of the forearm 14 presented to the observer 20.

Figure 2:
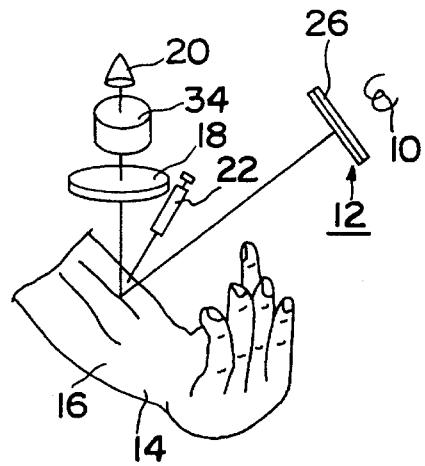
FIG. 2 shows the apparatus of FIG. 1 with the addition of an image intensifier.
Figure 4:
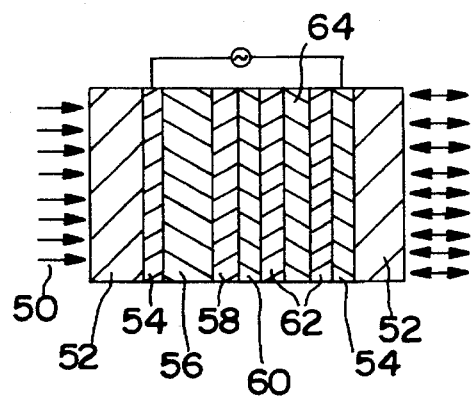
FIG. 4 shows an image intensifier unit of the prior art.

FIG. 2 shows the apparatus of FIG. 1 with an image intensifier 34 positioned between the eye of the observer 20 and the imaging means. An image intensifier suitable for this application is referenced in the specification, "Liquid Crystals, Applications and Uses." A preferred embodiment of this invention is an image intensifier utilizing a CdS photosensor with large sensitivity between 500 to 530 nm. (close to near infrared) matched with an Argon-ion light source having an output between 500 to 530 nm. (See FIG. 4 for location of photosensor).

Figure 3:
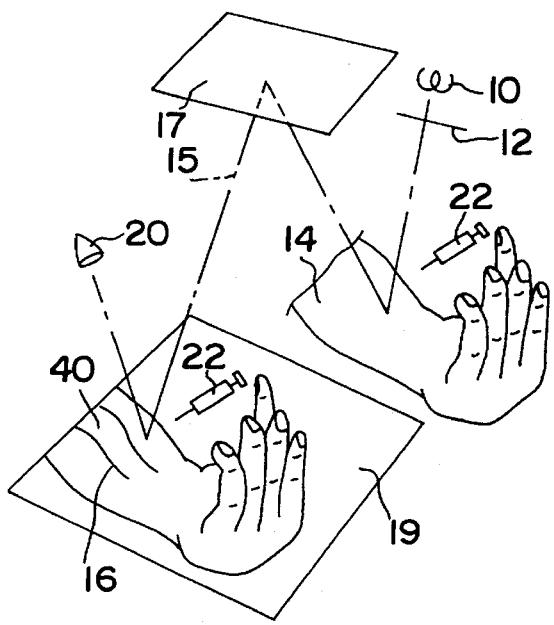
FIG. 3 shows an apparatus for presenting a reflected image simultaneously with the real object.

FIG. 3 shows yet another embodiment of the invention. A light beam from lamp 10 passes through narrow bandpass filter 12 and shines on the forearm 14.

The beam 15 reflected from forearm 14 is then reflected by overhead reflectance filter 17 and forms an image in reflectance filter 19 The operator can view side by side and simultaneously the forearm and the reflected image of the forearm 40 and thus be guided to insert the needle in the most appropriate location in the forearm. The combination lamp 10 and transmittance filter 12 emits radiation in the near infrared. The reflectance filters 17 and 19 are each a multilayer film on glass which absorbs all radiation other than the wavelength of beam 15.

As a further aid in the practice of this invention, a small LED emitting in the near infrared wavelength range, is located near the tip of the hypodermic needle and can thereby seen by the viewer as he positions the needle at the insertion point.

Other variations of this invention may be considered which are within the scope of this invention. For example, types of filters other than the polymer multilayered type may be used. A particular wavelength may be found to be advantageous in certain situations. I therefore wish to define my invention by the appended claims.

I claim:

1. A device for providing an enhanced view of venous structure in an area of a patient such as to aid a user to draw blood from said patient which comprises:

a lamp means for indicating said area with radiation having a plurality of wavelengths including a wavelength selected such that said radiation of said selected wavelength is absorbed in regions of said area where veins are located and reflected from other regions of said area where veins are not located;

a first transmittance filter interposed between said area and said lamp means which transmits substantially only radiation of said selected wavelength;

a focussing means having a support surface for supporting said first transmittance filter on said support surface;

said support surface of said focussing means being contoured to focus radiation of said selected wavelength onto said area of said patient;

an image forming means having a surface contoured for forming an image of said area adapted for viewing by said viewer;

a second transmittance filter supported on said contoured surface of said image forming means for transmitting only said radiations of said selected wavelength.

2. A device as in claim 1 which comprises means adapted for supporting said device on a head of a user.

3. A device as in claim 1 which comprises means adapted for supporting said device on a floor stand.

4. A device as in claim 1 wherein said means for irradiating comprises an Argon ion light source.

5. A device as in claim 1 which comprises a light source emitting radiation having said selected wavelength and adapted for a hypodermic needle such as to aid said user in positioning a tip of said hypodermic needle in an advantageous position for drawing blood from said area.

6. A device as in claim 1 wherein said selected wavelength is in a range of near infrared wavelengths.

7. A device as in claim 6 wherein said near infrared range is between 500 nm and 530 nm.

8. A device as in claim 1 which comprises an image intensifier adapted to be interposed between a rear surface opposite said support surface of said imaging means and said user.

9. A device as in claim 8 wherein:

said image intensifier comprises a CdS photosensor;

said means for irradiating has an Argon ion light source.

10. A device as in claim 1 which comprises:

said filter means being a reflectance filter that reflects said selected wavelength and effectively transmits all other wavelengths;

a mirror that reflects radiation having said selected wavelength and effectively prevents reflection of all radiation having other wavelengths; said filter means and said mirror operably positioned in combination with one another and said user such that an image of said irradiated area with delineated veins of said patient is viewable by said user while said user is simultaneously viewing said irradiated area directly such as to enable said viewer to accurately position a tip of a hypodermic needle at a desirable location in said area relative to said venous structure.

11. A device as in claim 5 wherein said light source is an LED.

12. A method for gaining intravenous access in an area of a patient which includes the steps:

irradiating said area from a source of radiation having a wavelength selected such that said radiation is absorbed in regions of said area where veins are located and reflected from other regions of said area where veins are not located;

filtering the emitting radiation such that only radiation of a selected wavelength is transmitted and all other wavelengths are blocked;

presenting a view of said irradiated area wherein venous structure in said area has been delineated by said irradiating step;

positioning a tip of said hypodermic needle at an appropriate location for gaining intravenous access using said view as a guide.

13. A method for gaining intravenous access in an area of a patient which includes the steps:

(a) positioning a device for aiding a user to gain intravenous access by viewing the venous structure in an area of a patient such as to aid said user to position a hypodermic needle for gaining intravenous access wherein said device comprises:

(i) means for irradiating said area with radiation having a wavelength selected such that said radiation is absorbed in regions of said area where veins are located and reflected from other regions of said area where veins are not located;

(ii) means for presenting a view of said irradiated area;

(b) irradiating said area from a source of radiation having a wavelength selected such that said radiation is absorbed in regions of said area where veins are located and reflected from other regions of said area where veins are not located;

and filtering the emitting radiation such that only radiation of a selected wavelength is transmitted and all wavelengths are blocked;

(c) presenting a view of said irradiated area wherein venous structure in said area has been delineated by said irradiating step;

(d) positioning a tip of said hypodermic needle at an appropriate location for gaining intravenous access using said view as a guide.

14. A method as in claim 13 wherein said means for irradiating comprises:

a lamp emitting radiation in a range of wavelengths including said selected wavelength;

a transmittance filter which transmits radiation having said selected wavelength and absorbs all other wavelengths in said range.

15. A method as in claim 14 wherein said selected wavelength is in a range of near infrared wavelengths.

16. A method as in claim 15 wherein said near infra red range is between 500 nm and 530 nm.

17. A method as in claim 13 wherein said means for presenting a view of said irradiated area comprises:

a transparent panel with a support surface adapted to face said irradiated area and be interposed between said irradiated area and said user;

a filter means mounted on said support surface adapted in operable combination with said irradiating means for delineating venous structure in a view of said area.

18. A method as in claim 17 wherein said filter means comprises a film that transmits radiation having said selected wavelength and blocks radiation having wavelengths different from said selected wavelength thereby presenting to said user a view of said irradiated area with venous structure further delineated.

19. A method as in claim 18 wherein said support surface is contoured such as to magnify a view of said irradiated area.

20. A method as in claim 18 wherein said device comprises an image intensifier adapted to be interposed between a rear surface opposite said support surface of said transparent panel said transparent panel and said user.

21. A method as in claim 20 wherein:

said image intensifier comprises a CdS photosensor;

said means for irradiating has an Argon ion light source.

22. A method as in claim 17 wherein said device comprises:

said filter means being a reflectance filter that reflects said selected wavelength and effectively transmits all other wavelengths;

a mirror that reflects said selected wavelength and effectively prevents reflectance of all other wavelengths;

said filter means and said mirror operably positioned in combination with one another and said user such that an image of said irradiated area with delineated veins of said patient is viewable by said user while said user is simultaneously viewing said irradiated area directly such as to enable said viewer to accurately position a tip of a hypodermic needle at a desirable location in said area relative to said veins.

23. A method as in claim 13 wherein said device comprises a light source emitting radiation having said selected wavelength and adapted for being secured to said hypodermic needle such as to aid said user in positioning a tip of said hypodermic needle in an advantageous position for drawing blood from said area.

24. A method as in claim 23 wherein said light source is an LED.

* * * * *

UNITED STATES PATENT AND TRADEMARK OFFICE
CERTIFICATE OF CORRECTION

PATENT NO.    : 5,519,208
DATED         : May 21, 1996
INVENTOR(S)   : Esparza, Joel and Smith, Robert S.

It is certified that error appears in the above-identified patent and that said Letters Patent is hereby corrected as shown below:

Column 5,
Line 18, delete "500" and insert -- 700 -- and delete "530" and insert -- 900 --.

Column 11,
Line 11, insert -- other -- between "all" and "wave-".
Line 29, delete "500" and insert -- 700 -- and delete "530" and insert -- 900 --.
Line 50, delete "said transparent panel".

Signed and Sealed this

Seventh Day of February, 2006

JON W. DUDAS
*Director of the United States Patent and Trademark Office*